(12) United States Patent
O'Connor et al.

(10) Patent No.: US 7,913,642 B2
(45) Date of Patent: Mar. 29, 2011

(54) FILM COATING MEDICAL DEVICES

(75) Inventors: Tim O'Connor, County Galway (IE); Dave McMorrow, Galway (IE); Gabriel Sobrino, County Galway (IE); Liam Ward, County Galway (IE); Noel Hynes, County Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 209 days.

(21) Appl. No.: 11/858,347

(22) Filed: Sep. 20, 2007

(65) Prior Publication Data

US 2008/0095921 A1    Apr. 24, 2008

Related U.S. Application Data

(60) Provisional application No. 60/852,979, filed on Oct. 20, 2006.

(51) Int. Cl.
*B05C 1/00* (2006.01)

(52) U.S. Cl. ........ 118/246; 427/2.1; 427/2.24; 427/356; 427/359; 427/2.25; 427/430.1; 427/435; 427/443.2

(58) Field of Classification Search .................. 427/2.24, 427/2.1
See application file for complete search history.

(56) References Cited

U.S. PATENT DOCUMENTS

| 2,821,158 A | 1/1958 | Leonard et al. |
| 3,990,395 A | 11/1976 | Evans et al. |
| 4,838,976 A | 6/1989 | Sato |
| 2005/0074544 A1 | 4/2005 | Pacetti et al. |
| 2005/0079274 A1 | 4/2005 | Palasis et al. |
| 2007/0281072 A1* | 12/2007 | O'Connor et al. .............. 427/2.1 |

FOREIGN PATENT DOCUMENTS

WO    2005/091834    10/2005

OTHER PUBLICATIONS

International Search Report and Written Opinion in PCT/US2007/020326, mailed Mar. 13, 2008.
IP.com Electronic Publication "Method of Controlling Stent/Coating Film Interference in Roll Coating Process" dated May 9, 2006, www.ip.com; IP.com No. IPCOM000136192D.

* cited by examiner

*Primary Examiner* — Michael Barr
*Assistant Examiner* — Andrew Bowman
(74) *Attorney, Agent, or Firm* — Vidas, Arrett & Steinkraus

(57) ABSTRACT

The present invention relates to a coating assembly and methods that employ the coating assembly to control the thickness of therapeutic or other coatings delivered to a medical device during a coating process. In one embodiment the coating assembly may include a coating plate having a coating transfer surface and a shoulder having a first height, a mandrel moveable over the coating transfer surface, and a coating dispenser positioned in fluid communication with the coating transfer surface. The invention also includes a method of coating a medical device. This method may include placing a medical device on a mandrel, dispensing coating onto a coating transfer surface of a coating plate, moving the mandrel and the medical device over the coating transfer surface of the coating plate so that coating resident on the coating transfer surface transfers to an exposed surface of the medical device, and removing the medical device from the mandrel.

12 Claims, 5 Drawing Sheets

FILM COATING MEDICAL DEVICES

RELATED APPLICATION

This application claims benefit of Provisional Application No. 60/852,979, filed Oct. 20, 2006, which is incorporated herein in its entirety.

TECHNICAL FIELD

The present invention generally relates to coating medical devices. More specifically, the present invention relates to devices and methods that control the thickness of therapeutic or other coatings delivered to some or all surfaces of a workpiece during a coating process.

BACKGROUND

Coating workpieces is an often repeated procedure in contemporary manufacturing. Workpieces may be coated by methods that include tumble coating, spray coating, dip coating, and electrostatic spraying. During each of these procedures coating is applied to the workpiece prior to the workpiece being used for an intended purpose.

When the workpiece is formed partially or completely out of lattice struts or some other open framework, each of the faces of these struts or framework is exposed to the coating and coated during the coating methods listed above. By exposing each face of the workpiece to the coating being applied, each exposed face will be covered during the coating process.

When the workpiece being coated is an implantable medical device, such as a stent, all faces of the struts that comprise the stent are coated when using the coating systems identified above. For example, when dip coating is used, each face of the stent struts will be exposed to the coating as it is dipped into a vat of coating. This coating will remain when the stent is removed from the dip and will dry on each face of the struts. Coating may also remain in the spaces between the struts. This phenomenon is sometimes called "webbing." Here, not only are the individual struts covered, but some or all of the spaces between the struts are spanned by the coating as well.

BRIEF DESCRIPTION

The present invention regards coating a workpiece by transferring coating from a film of coating to a workpiece. The film of coating may be resident on a transfer surface of a coating assembly. This transfer surface may receive the coating from a dispenser that dispenses coating to the transfer surface of the coating assembly so as to form a film on the surface. The coating assembly can comprise a mandrel configured to support a workpiece such as a medical implant, a coating plate positioned adjacent the mandrel and in fluid communication with a coating dispenser, and a shoulder sized and configured to position the mandrel a distance away from the coating transfer surface of the coating plate. The coating assembly and/or mandrel may also include a biasing member that urges the mandrel and shoulder towards one another. In use, a workpiece, such as a stent, may be placed on the mandrel and a measured amount of coating may be placed on the transfer surface so as to form a film of coating on the transfer surface. The mandrel may be moved back and forth over the transfer surface of the coating assembly to interface the workpiece with the coating. Once the transfer occurs, the workpiece may be removed. The thickness of the coating that ultimately resides on the workpiece may be controlled by: metering or controlling the amount of coating dispensed to the transfer surface; by mechanical means that squeegee the coating on the transfer surface; and by changing the distance between the mandrel and the transfer surface. It may be changed in other ways as well.

The present invention also regards a method of coating a workpiece by transferring coating from a transfer surface of a coating assembly to the workpiece. The method may include positioning a workpiece on a mandrel, depositing coating on a transfer surface of a coating assembly, waiting a period of time, and interfacing the workpiece with the coating such that coating is transferred to the workpiece in order to coat the workpiece. This method may also include repeating the procedure, performing more or other steps, and adding an additional coating.

The invention may be embodied in numerous other devices and through numerous other methods and systems. The following detailed description, which, when taken in conjunction with the annexed drawings, discloses examples of the invention. Other embodiments, which incorporate some or all of the features, are also possible.

BRIEF DESCRIPTION OF THE DRAWINGS

Referring to the drawings, which form a part of this disclosure.

DETAILED DESCRIPTION

Figure 1:
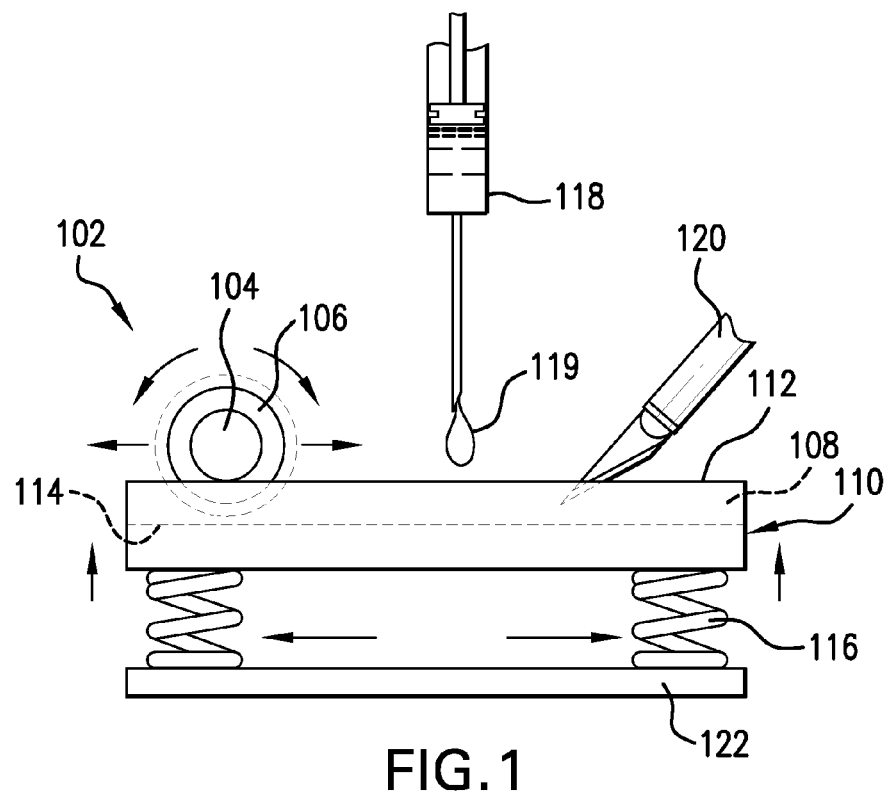
FIG. 1 shows a coating assembly that may be employed in accord with the present invention.

A coating assembly 102 in accord with the present invention is shown in FIG. 1. There, a coating assembly 102 is shown having a mandrel 104, a doctor blade 120, a coating plate 110, and a base 122. Also visible in FIG. 1 is a coating dispenser 118, which may be a syringe, an automatic injector, a micro-pipette, a needle, or a spray nozzle. The coating plate 110 of the coating assembly 102 has a transfer surface 114 and shoulder 112 on which the mandrel 104 is configured to translate and rotate. The base 122 is coupled to the coating plate 110 with a springs or biasing members 116. Although the coating plate is biased in this example with two springs, other arrangements are possible. For example, any number of springs may be used, only the mandrel 104 may be biased (FIG. 2), both the mandrel 104 and base 122 may be biased, and/or the mandrel 104 and base 122 may be provided without biasing members. These biasing elements may be sized to maintain contact between the shoulder 112 and the mandrel 104 when the mandrel 104 slides back and forth across the coating plate 102. Also visible in FIG. 1 is a film of coating 108. This film has been formed from coating droplets 119 dispensed from coating dispenser 118 and by the movement of the doctor blade 120 over the coating. The film thickness may be further regulated by any suitable metering device including rollers, rods, pins, straight edges, serrated edges, and coils, which are not shown. Because the mandrel 104 translates and rotates along the shoulder 112 of the coating assembly, the depth of the coating applied to the medical device can also be regulated by the height of the shoulder.

When the system of FIG. 1 is used coating may be dispensed from the dispenser 118 onto the transfer surface 114. The coating may then be smoothed, squeegeed, or otherwise regulated over the transfer surface by the doctor blade 120. The doctor blade may be moved in any desired direction or directions. Once present on the transfer surface 114, the mandrel 104 may be slid along the shoulder 112 of the coating plate in order to interface the medical device 106 with a film of coating resident on the coating plate. As the mandrel moves across the shoulder it may rotate, placing the exposed surfaces of the medical device in contact with the film of coating. The amount of coating transferred to the medical device may depend upon the depth in which the medical device is dipped into the coating. This depth may be adjusted by controlling the film thickness and by adjusting the height in which the mandrel is positioned above the transfer surface 114. Various dispensing process parameters may also be controlled to extend control over the thickness of the coating placed on the medical device. For example, coating solution viscosity and volume can each be varied to adjust the resulting height or thickness of coating resident on the medical device.

In addition to adjusting coating viscosity and the other identified parameters, coating thickness may also be adjusted by varying the amount of time taken to perform the steps of the coating procedure. For instance, the amount of time that the workpiece may be in contact with the coating to be transferred to the workpiece can be quite long even if the coating is highly viscous. Moreover, the contact time can also be adjusted to suit the size of the medical device. Still further, the amount of time between when the coating is dispensed onto the transfer surface 114 and when the medical device interfaces with it may also be adjusted to minimize or maximize the evaporation of the coating placed on the surface. In other words, if a more highly concentrated coating is desired, the coating may be allowed to reside on the transfer surface for a longer period of time to allow solvents in the coating to evaporate. Thus, as dwell time increases here, the coating becomes more concentrated. Comparatively, if a less concentrated coating is needed, the dwell time between dispensing from the dispenser 118 and application to the medical device 106 will be shortened in order to minimize evaporation.

Any desired amount of coating may be dispensed from the dispenser, for instance, a suitable range may include, but is not limited to 5 to 50 microlitres. The amount of coating which is deposited on the work piece may depend upon a number of parameters such as the surface area of the work piece, the immersion depth of the work piece in the coating film, translation and rotational speeds, and the properties of the coating. In one example, 10 microlitres of coating was dispensed from the dispenser thereby resulting in 0.05 microlitres of coating being deposited on the work piece.

In some instances, coating may remain on the coating transfer surface. In these instances, the coating transfer surface may be cleaned, manually or automatically, with a suitable cleaning tool after each coating cycle.

Figure 2:
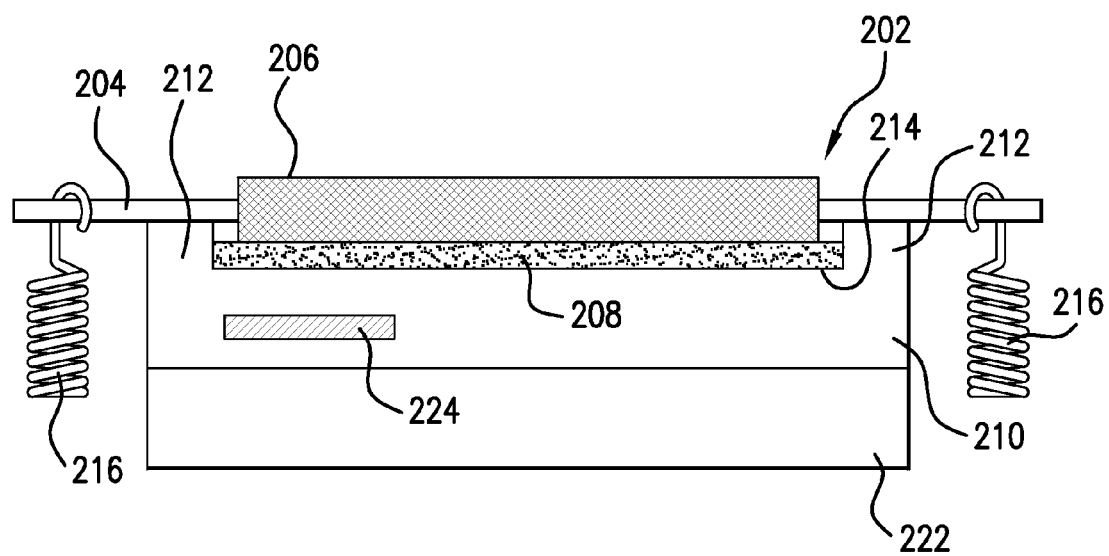
FIG. 2 shows a front-view of a coating plate and mandrel that may be employed in accord with the present invention.

FIG. 2 shows a coating assembly 202 having a medical device 206 positioned on a mandrel 204 in contact with shoulder 212 of coating plate 210. Also visible in the figure are a temperature control mechanism 224 in the coating plate 210, biasing members 216, a base 222, and the transfer surface 214 of the coating plate 210. As can be seen in this figure, the film of coating 208 on the transfer surface 214 is in contact with the medical device 206 when the mandrel is in contact with the shoulders 212 of the coating plate 210.

In FIG. 2, the mandrel 204 may be a cylindrical pin-shaped support and may be made of any suitable metallic and/or polymeric material such as stainless steel or tungsten carbide. Preferably the mandrel 204 may be precision ground to maintain precision tolerances. However, other suitable manufacturing techniques include center-less grinding, cast molding, and sintering. The outer surface of the mandrel 204 may also be coated with a non-stick material such as PTFE and Teflon™. Still further, the mandrel 204 may be sized such that it is slightly larger than the medical device 206 so that the medical device 206 can be secured with friction to the mandrel. For example, if a tubular stent is being coated, the outer diameter of the mandrel 204 may be slightly larger than the stent's inner diameter. This over-sizing will promote a secure attachment between the mandrel and the stent during the coating process. This may be used to reduce wear and limit damage to coatings that may be located on an inner diameter of the medical device 206.

As to the coating plate 210 of FIG. 2, it may be a generally flat plate having one or more shoulders 212 to guide the mandrel. It may contain an essentially flat transfer surface and may contain a temperature control mechanism 224, such as a heater or cooler, to heat or cool the coating plate 210. The coating plate 210 may be preferably made of a material having low wettability. For example, the coating plate 210 may be made of stainless steel, PTFE, glass, and ceramic. The shoulders of the coating plate are preferably higher than the thickness of the film of coating 208 that may be placed on the transfer surface of the coating plate 210.

The mandrel 204 and shoulders 212 of the coating plate 210 may be positioned in close proximity to one another or may contact one another during the coating process and otherwise. They may be urged together under the forces generated by the biasing members 216. If there is a clearance between the mandrel 204 and shoulders 212, any calculations based upon the thickness of the film 208 may be adjusted by this clearance distance. By doing so, a constant or known distance may be maintained between the mandrel and the transfer surface as the mandrel moves back and forth over the transfer surface. Moreover, the biasing members 216 may limit the influence of bearing clearances and other machine moving part tolerances on the final coating thickness. While the biasing members 216 are shown as springs, other configurations may also be used. For example, pneumatic, hydraulic, and suspended weight techniques may be used as alternatives to springs.

Figure 3:
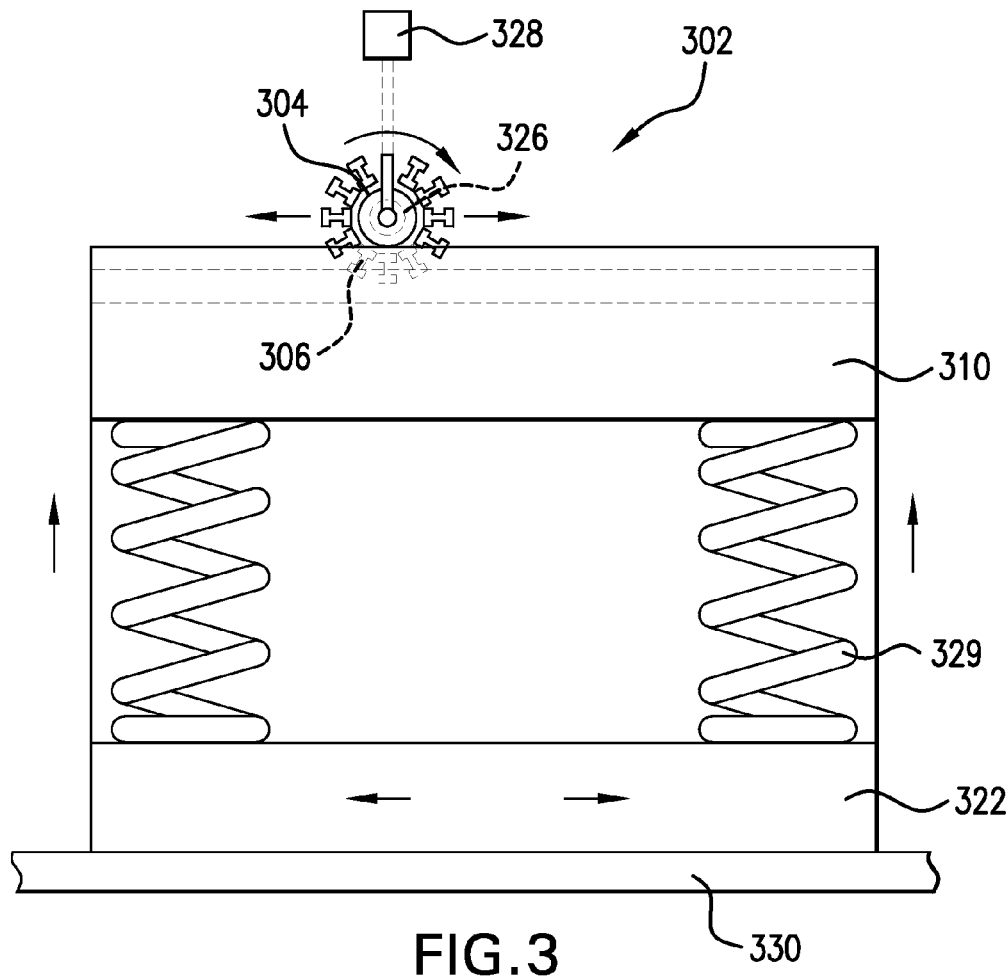
FIG. 3 shows a side-view of another coating plate and mandrel that may be employed in accord with the present invention.

FIG. 3 is a side view of a coating assembly 302 in accord with the present invention. The coating assembly 302 in this figure includes a mandrel 304, a coating plate 310, a base 322, and biasing elements 329. Also shown in FIG. 3 are a motor 326, a first linear actuator 328, a second linear actuator 330, and a medical device 306. The coating assembly 302 in this figure can act to move the mandrel 304 over the coating as well as to automatically rotate it at the same time. While the coating is being applied, the motor 326 can be used to rotate the medical device 306 in a clockwise and/or counterclockwise direction through the coating film thickness located on the coating plate 310. The mandrel 304 may be connected to the linear actuator 328 via a support. The linear actuator 328 may move the mandrel linearly, in both directions, to facilitate coating. A second linear actuator 330 may be connected to the base and or directly to the coating plate 310 to move the coating plate 310 linearly, in both directions. Thus, both the coating plate and the mandrel may move in order to change the relative position of the medical device to the coating film on the coating plate. The linear actuators 328, 330 may be any hydraulic, pneumatic, electrical, or mechanical actuators. These actuators may be controlled during the coating process to achieve desired coating thicknesses. For example, the rotational speed and linear speeds may be adjusted.

Figure 4:
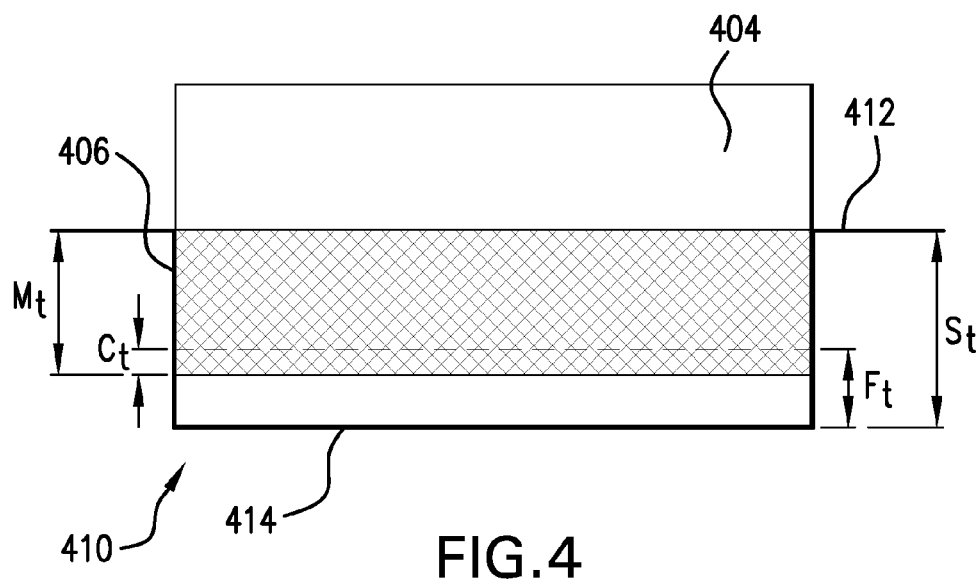
FIG. 4 shows an enlarged view of a transfer surface of a coating plate slot with arrows illustrating the medical device thickness, the coating thickness, the film thickness, and the coating plate depth in accord with the present invention.

FIG. 4 shows an enlarged view of a transfer surface 414 of a coating plate 410 in accord with the embodiments of the present invention. FIG. 4 includes arrows which show the effective depth of the transfer surface, the medical device thickness, the film thickness, and the coating thickness. The transfer surface depth ($S_t$) may be determined by the height of the shoulder 412. The medical device wall thickness ($M_t$) may be determined by the radial thickness of the outer wall of the medical device. The coating film thickness ($F_t$) may be achieved via adjustment of various depositing and metering parameters. The final coating thickness ($C_t$), or interference, may be the determined by the overlap of the medical device thickness ($M_t$) and the metered film thickness ($F_t$). For example:

If, ($S_t$)=85 micrometers; ($M_t$)=70 micrometers; and ($F_t$)=25 micrometers, then, ($C_t$)=10 micrometers In this example the final coating thickness ($C_t$) is approximately 10 micrometers. Thus, by maintaining the gap between the coating plate 410 and the medical device 406 (which is mounted on mandrel 404), the final coating thickness of 10 micrometers may be maintained for an entire batch. In the example, 10 micrometers is the final coating thickness, however, any desired uniform thickness of coating may be applied to a target surface of a medical device 406. For example, suitable ranges for medical device (e.g., 8 mm stents) coating thicknesses may be approximately 1-50 micrometer coating thicknesses and 1-50 microgram coating weights.

Larger coating thicknesses and higher coating weights may also be produced. For instance, in a single machine cycle, several layers of coating may be applied via additional rotations of the medical device.

Figures 5A, 5B:
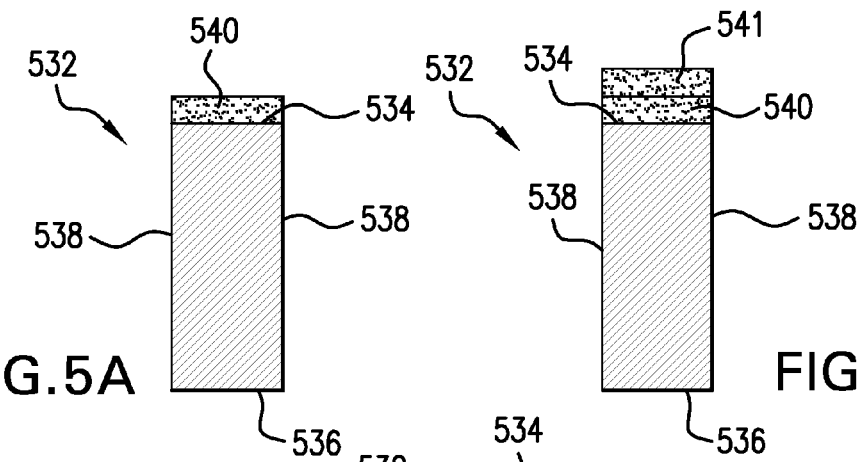
FIG. 5A is a cross-sectional view of a portion of a coated strut from a medical device that has been coated in accord with the present invention.
FIG. 5B is a cross-sectional view showing the coated strut of FIG. 5A after a second coating has been applied in accord with the present invention.

FIG. 5a is a side sectional view of a strut 532 of a stent that may be coated in accord with the present invention. The strut 532 in FIG. 5a has an inner surface 536, an outer surface 534, and two cut faces 538. Also shown on the strut 532 is a coating 540. As can be seen, the coating 540, covers only one face of the strut 532.

FIG. 5b shows an example of how a second coating 541 may also be applied in accord with the invention. In FIG. 5b, a first and second coating 540, 541 have been applied to the strut 532. As can be seen, the first coating 540, is in contact with the strut 532 while the second coating 541 is in contact with the first coating 540 and further covers the outer surface 534 of the strut. This second coating 541 may be applied in accord with the processes and methods of the present invention. It may also be applied with different methods and processes.

In this example, as well as with the others described herein, if a second coating is employed this coating may comprise the same materials as the first coating and it may differ from the materials used for the first coating. In still other examples, which are not shown, the coating may be applied in other patterns as well. For example, it may be applied to opposing cut faces and not the outer surface, likewise it may be applied to both cut faces and the outer surface. In the exemplary embodiment, the outer surface is coated and the two cut faces as well as the inner surface are not.

Figure 5C:
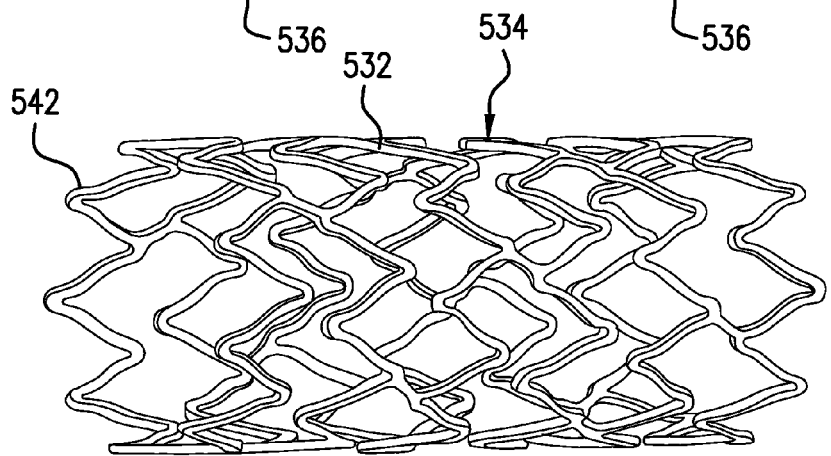
FIG. 5C is a side-view of an arterial stent, which is a medical device that may be coated in accord with the present invention.

FIG. 5c is a side view of an implantable aortic stent 542 including a lattice portion 534 having struts 532 that may be coated in accord with the invention. The stent may be porous or have portions thereof that are porous. The struts 532 shown in FIGS. 5a and 5b are struts 532 that may comprise and make up this stent. While the workpiece shown in these initial figures is a stent, many other workpieces may be coated in accord with the invention.

For example, other medical devices that may be coated include filters (e.g., vena cava filters), stent grafts, vascular grafts, intraluminal paving systems, implants and other devices used in connection with drug-loaded polymer coatings. Likewise, the workpeice may not be an implantable medical device but may, instead, be another piece that needs to be coated only on certain pre-selected surfaces. In some instances these medical devices or other workpieces may be made from conductive materials and in other instances they may not be. For example, they may be made from polymers or ceramics.

The medical implants themselves may be self-expanding, mechanically expandable, or hybrid implants which may have both self-expanding and mechanically expandable characteristics. Mechanical or expandable medical devices may aid in traversing the narrower peripheral arteries and allow for expansion to the appropriate size/geometry when the targeted vessel lumen is reached.

The medical implant may be made from a variety of materials including plastics and metals.

Figures 6A, 6B:
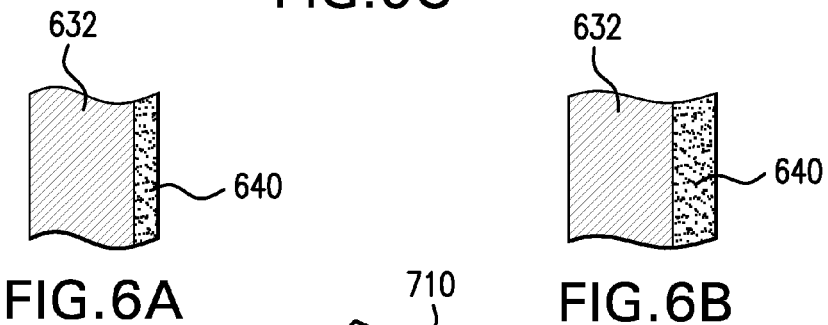
FIG. 6A is a cross-sectional view of a portion of a coated strut from a medical device in which a long dwell time is used in accord with the present invention.
FIG. 6B is a cross-sectional view of a portion of a coated strut from a medical device in which a short dwell time is used in accord with the present invention.

FIGS. 6A and 6B show examples of coated struts 632 having different coating 640 thicknesses. The final coating thickness may differ depending upon dwell times periods used throughout a coating process. For example, the coating process may be suspended temporarily after depositing coating on the coating plate. Further, the coating process may be suspended temporarily after regulating coating with the metering device. Although suspension of the coating process for a dwell time period may be optional, the dwell time period may be another controllable parameter that may be used in accordance with the embodiments of the present invention. As is evident in FIG. 6A, longer dwell times may result in a larger degree of evaporation of solvents from the coating solution. Alternatively, as seen in FIG. 6B, shorter dwell times may result in minimal evaporation. Thus, the coating 640 in FIG. 6B is thicker. Adjustments made to the dwell times may correlate directly to the degree of coating film deposited on the surfaces of the medical device. Any suitable dwell time periods may be used. For example, dwell time periods between 0 and 300 seconds may be used.

It may be desirable to change the dwell time in order to shorten or lengthen the machine cycle. For instance, if the cycle time is approximately one minute plus the dwell time, the cycle time can be varied accordingly by changing the dwell time. In other examples, the cycle time can be altered or optimized depending on selected machine speed settings. In still other instances, the dwell time may be changed by varying the coating formulation or the types of solvents used. Dwell time adjustment may enable fast evaluation of alternative coating formulations and may also allow a wider range of materials to be used as the dwell time allows excess solvent to evaporate.

Figure 7:
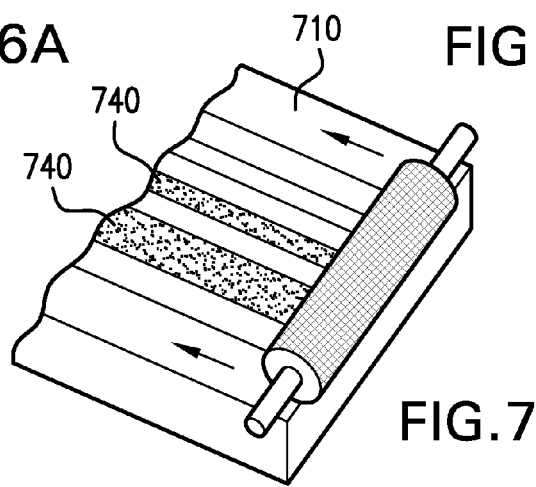
FIG. 7 shows a coating plate with different coatings deposited adjacent one another in accord with the present invention.

Turning to FIG. 7, this embodiment illustrates a coating plate 710 having stripes of different coating 740 deposited on a surface thereof. In this example, the two coatings 740 are different, however, other arrangements are possible. For example, a plurality of stripes of the same or different coatings may be used. Thus, by using this configuration, a medical device interfaced with these stripes may receive different coatings, the same coating, and the same coating but in different concentrations during coating with the coating assemblies described herein.

Figure 8:
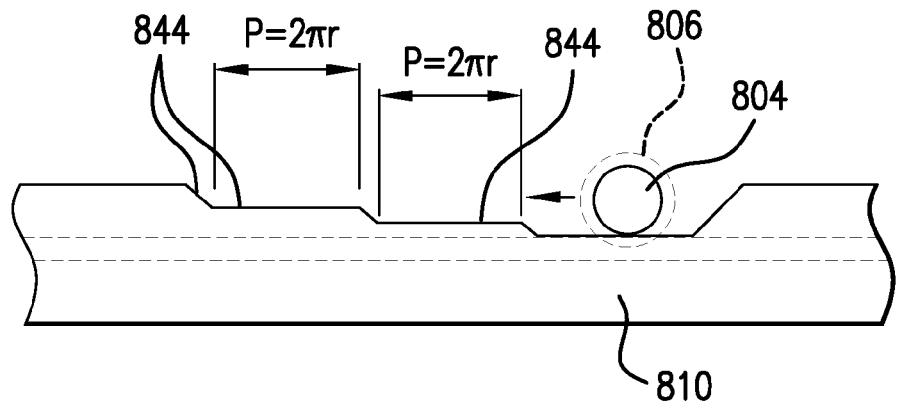
FIG. 8 shows a coating plate having stepped shoulders in accord with the present invention.
Figure 9:
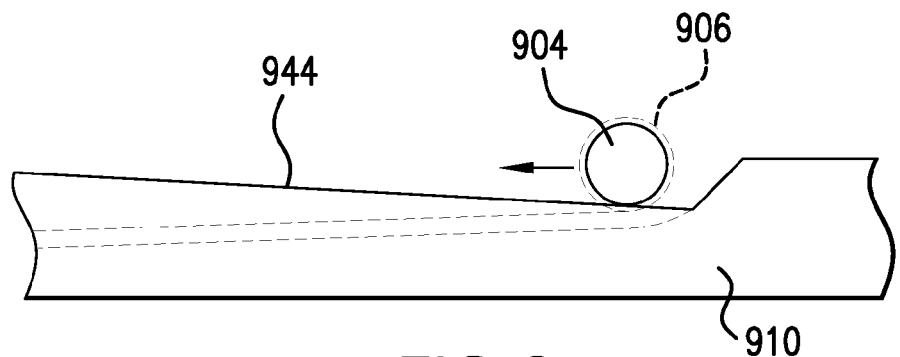
FIG. 9 shows another coating plate having a sloped shoulder in accord with the present invention.
Figure 10:
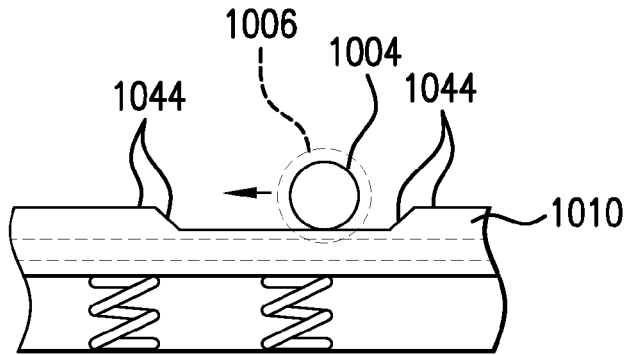
FIG. 10 shows another coating plate having a two-tier shoulder configuration in accord with the present invention.

FIGS. 8-10 shows various mandrels 804, 904, 1004, medical device 806, 906, 1006, and coating plates 810, 910, 1010 that may be used in accord with the embodiments of the invention. In these embodiments, the coating plates may have shoulder surfaces configured to maintain a constant immersion depth of the medical device within the coating film thickness.

As seen in FIG. 8, the plurality of shoulder surfaces 844 may create a series of steps. Each step comprises a generally flat section. The length of the flat section may be equal to the circumferential distance (2*PT*r) of the medical device 806. In other words, the medical device 806 may travel one full rotation over the length of the flat section.

In FIG. 9, the coating plate 910 may have a shoulder surface 944 that may slope upwards. In other words, when traveling from left to right, the gradient of the shoulder increases.

FIG. 10 shows yet another embodiment of the coating plate 1010. In this embodiment the coating plate may have first and second shoulders surfaces 1044 to facilitate the application of thicker coatings.

As the medical device moves with respect to the coating plates of FIGS. 8-10 from left to right, the mandrel may rotate with respect to the shoulder. Accordingly, the medical device, which extends into the slot of the coating plate, may be rotated to accumulate coating. Therefore, in each successive step or revolution, the depth the medical device is immersed in the solution may change. Consequently, the shoulder surfaces may be provided to move the medical device away from the slot a suitable distance so that a constant immersion depth of the medical device may be maintained.

FIGS. 8-10 are exemplary and other arrangements are plausible. For example any number or combinations of shoulder surfaces may be used. Moreover, the length of the coating plate may be varied to permit any number of revolutions in a single machine cycle.

Figure 11:
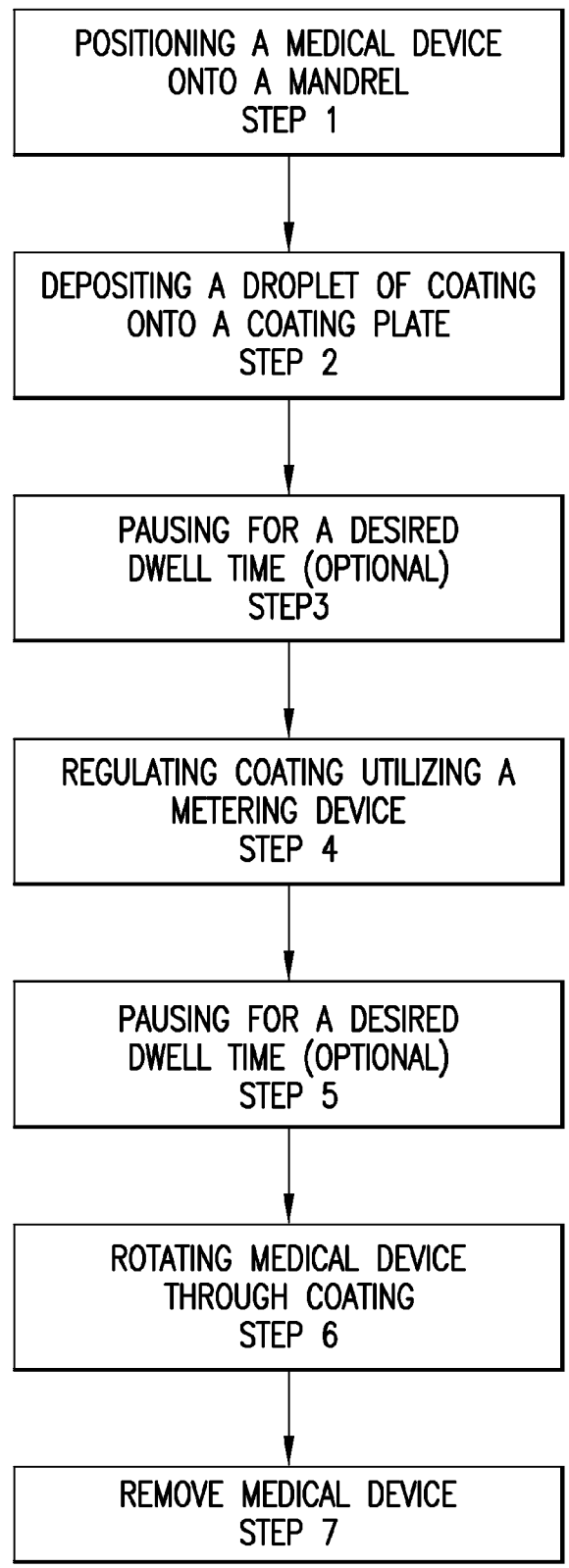
FIG. 11 shows a flow chart illustrating method steps that may be employed in accord with the present invention.

FIG. 11 shows a flow chart including method steps that may be employed with embodiments of the present invention to coat a target portion of a medical device. In the example of FIG. 11, Step 1 may include positioning a medical device on a mandrel. Step 2 may include depositing coating onto a coating plate. Step 3 may include pausing for a desired dwell time period. Step 4 can include regulating the coating thickness on the coating plate utilizing a metering device. Step 5 may include again pausing for a desired dwell time period. Step 6 can include rotating the medical device through the coating. Step 7 may include removing the medical device from the coating and the mandrel.

In alternative embodiments, not shown, the sequence of steps may be reordered and steps may be added or removed. The steps may also be modified. For example, as the medical device is rotated through the coating on the coating plate, additional coating may also be dispensed onto the plate. The steps may also be repeated in continuous fashion.

While various embodiments have been described, other embodiments are plausible. It should be understood that the foregoing descriptions of various examples of the coating assembly and methods employing the coating assembly are not intended to be limiting, and any number of modifications, combinations, and alternatives of the examples may be employed to facilitate the effectiveness of the coating of target surfaces of the workpiece.

The coating, in accord with the embodiments of the present invention, may comprise a polymeric and or therapeutic agent formed, for example, by admixing a drug agent with a liquid polymer, in the absence of a solvent, to form a liquid polymer/drug agent mixture. A suitable list of drugs and/or polymer combinations is listed below. The term "therapeutic agent" as used herein includes one or more "therapeutic agents" or "drugs." The terms "therapeutic agents" or "drugs" can be used interchangeably herein and include pharmaceutically active compounds, nucleic acids with and without carrier vectors such as lipids, compacting agents (such as histones), viruses (such as adenovirus, adenoassociated virus, retrovirus, lentivirus and α-virus), polymers, hyaluronic acid, proteins, cells and the like, with or without targeting sequences.

Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; anti-proliferative agents such as enoxaprin, angiopeptin, rapamycin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/anti-proliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the insertion site. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMPs"). The known proteins include BMP-2, BMP-3, BMP-4, BMP-5, BMP-6 (Vgr-1), BMP-7 (OP-1), BMP-8, BMP-9, BMP-10, BMP-1, BMP-12, BMP-13, BMP-14, BMP-15, and BMP-16. Currently preferred BMPs are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNAs encoding them.

As stated above, coatings used with the exemplary embodiments of the present invention may comprise a polymeric material/drug agent matrix formed, for example, by admixing a drug agent with a liquid polymer, in the absence of a solvent, to form a liquid polymer/drug agent mixture. Curing of the mixture typically occurs in-situ. To facilitate curing, a cross-linking or curing agent may be added to the mixture prior to application thereof. Addition of the cross-linking or curing agent to the polymer/drug agent liquid mixture must not occur too far in advance of the application of the mixture in order to avoid over-curing of the mixture prior to application thereof. Curing may also occur in-situ by exposing the polymer/drug agent mixture, after application to the luminal surface, to radiation such as ultraviolet radiation or laser light, heat, or by contact with metabolic fluids such as water at the site where the mixture has been applied to the luminal surface. In coating systems employed in conjunction with the present invention, the polymeric material may be either bioabsorbable or biostable. Any of the polymers described herein that may be formulated as a liquid may be used to form the polymer/drug agent mixture.

The polymer used in the exemplary embodiments of the present invention is preferably capable of absorbing a substantial amount of drug solution. When applied as a coating on a medical device in accordance with the present invention, the dry polymer is typically on the order of from about 1 to about 50 microns thick. In the case of a balloon catheter, the thickness is preferably about 1 to 10 microns thick, and more preferably about 2 to 5 microns. Very thin polymer coatings, e.g., of about 0.2-0.3 microns and much thicker coatings, e.g., more than 10 microns, are also possible. It is also within the scope of the present invention to apply multiple layers of polymer coating onto a medical device. Such multiple layers are of the same or different polymer materials.

The polymer of the present invention may be hydrophilic or hydrophobic, and may be selected from the group consisting of polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers.

Coatings from polymer dispersions such as polyurethane dispersions (BAYHYDROL®, etc.) and acrylic latex dispersions are also within the scope of the present invention. The polymer may be a protein polymer, fibrin, collagen and derivatives thereof, polysaccharides such as celluloses, starches, dextrans, alginates and derivatives of these polysaccharides, an extracellular matrix component, hyaluronic acid, or another biologic agent or a suitable mixture of any of these, for example. In one embodiment of the invention, the preferred polymer is polyacrylic acid, available as HYDROPLUS® (Boston Scientific Corporation, Natick, Mass.), and described in U.S. Pat. No. 5,091,205, the disclosure of which is hereby incorporated herein by reference. U.S. Pat. No. 5,091,205 describes medical devices coated with one or more polyisocyanates such that the devices become instantly lubricious when exposed to body fluids. In another preferred embodiment of the invention, the polymer is a copolymer of polylactic acid and polycaprolactone.

The examples described herein are merely illustrative, as numerous other embodiments may be implemented without departing from the spirit and scope of the exemplary embodiments of the present invention. Moreover, while certain features of the invention may be shown on only certain embodiments or configurations, these features may be exchanged, added, and removed from and between the various embodiments or configurations while remaining within the scope of the invention. Likewise, methods described and disclosed may also be performed in various sequences, with some or all of the disclosed steps being performed in a different order than described while still remaining within the spirit and scope of the present invention.

What is claimed is:

1. A coating assembly for coating an outside surface of a medical device, the assembly comprising:
    a coating plate having a coating transfer surface and a shoulder having a first height;
    a mandrel moveable over the coating transfer surface; and
    a coating dispenser positioned in fluid communication with the coating transfer surface,
    wherein the shoulder is positioned and sized to support the mandrel as it moves over the coating transfer surface,
    wherein the mandrel is free to rotate as moves over the coating transfer surface,
    wherein as the mandrel moves over the coating surface in contact with the shoulder of the coating plate, the mandrel is positioned such that a medical device on the mandrel will interface with coating resident on the coating transfer surface.

2. The assembly of claim 1, further comprising a doctor blade positioned over the coating transfer surface.

3. The assembly of claim 2 wherein the doctor blade and the coating transfer surface may move relative to each other.

4. The assembly of claim 1, wherein the mandrel is tubular.

5. The assembly of claim 1, wherein the shoulder has a second height, the second height smaller than the first height.

6. The assembly of claim 1, wherein the mandrel is coated with a coating.

7. The assembly of claim 1, wherein the coating transfer surface comprises a substantially flat plate.

8. The assembly of claim 1, further comprising a base and a biasing member, the biasing member coupling the base to the coating plate.

9. The assembly of claim 1, wherein the coating transfer surface contains a first coating and a second coating, the first and second coating positioned adjacent to each other on the coating transfer surface.

10. The assembly of claim 5, wherein the mandrel has an outer circumference and the length of the shoulder at the first height is at least the circumference of the mandrel and the length of the shoulder at the second height is at least the circumference of the mandrel.

11. The assembly of claim 1, wherein a film of coating having a therapeutic is positioned on the coating transfer surface.

12. The assembly of claim 1, wherein a stent is positioned on the mandrel.

* * * * *